United States Patent [19]

Epinette

[11] Patent Number: 4,718,915
[45] Date of Patent: Jan. 12, 1988

[54] FEMORAL COMPONENT OF A HIP PROSTHESIS

[76] Inventor: Jean-Alain Epinette, 27 rue Lamandin, 62700 Bruay-en-Artois, France

[21] Appl. No.: 844,551

[22] Filed: Mar. 27, 1986

[30] Foreign Application Priority Data

Mar. 27, 1985 [FR] France .............................. 85 04548

[51] Int. Cl.⁴ ............................................... A61F 2/32
[52] U.S. Cl. .......................................... 623/23; 623/18
[58] Field of Search ..................................... 623/16-23

[56] References Cited

U.S. PATENT DOCUMENTS

| | | | |
|---|---|---|---|
| 4,163,290 | 8/1979 | Averett | 3/1.913 |
| 4,530,115 | 7/1985 | Müller et al. | 623/23 |
| 4,536,894 | 8/1985 | Galante et al. | 623/23 |

FOREIGN PATENT DOCUMENTS

| | | |
|---|---|---|
| 0041591 | 12/1981 | European Pat. Off. . |
| 0085147 | 8/1983 | European Pat. Off. . |
| 0128036 | 12/1984 | European Pat. Off. . |
| 0131178 | 1/1985 | European Pat. Off. . |
| 0149527 | 7/1985 | European Pat. Off. . |
| 2839093 | 3/1980 | Fed. Rep. of Germany . |
| 1278359 | 10/1961 | France . |
| 0050533 | 4/1982 | France | 623/23 |
| 8403037 | 1/1984 | PCT Int'l Appl. | 623/23 |
| 2153233 | 1/1985 | United Kingdom | 623/23 |

Primary Examiner—Richard J. Apley
Assistant Examiner—David Isabella
Attorney, Agent, or Firm—Perry Carvellas

[57] ABSTRACT

The femoral component of a hip prosthesis comprises a shaft, from the upper face of which projects a neck carrying a spherical head intended to seat in a cotyloid component. The shaft, which tapers toward a lower end, is curved to connect the neck to the axis of the femur, and comprises, in its upper part, two planer frontal faces, each cut by dovetail-shaped channels. Two packing pieces, an anterior packing piece and a posterior packing piece, engage these faces through bearing faces. Towards the lower part of each packing piece, a stud with a frustoconical head engages the dovetail-shaped channel to guide the packing piece during the installation of the femoral component and to permit a millimetric displacement of the core relative to the packing pieces and to the femur, in response to the variations in the verticle load on the prosthesis. The packing pieces have external convex faces. The external convex faces of the packing pieces are rough to assure connection with the spongy bone as it grows.

13 Claims, 6 Drawing Figures

4,718,915

FEMORAL COMPONENT OF A HIP PROSTHESIS

BACKGROUND OF THE INVENTION

Field of the Invention

The invention concerns a femoral component of a hip prosthesis intended to be implanted without cement, and comprising a shaft adapted to be driven into the medullary cavity of the femur after removal of the head by cutting the neck, said shaft tapering to a lower end from an upper end, from which projects a neck carrying an added spherical head adapted to form a ball-and-socket joint with a cotyloid component so as to reproduce the original natural joint.

(b) Description of the Related Art

It is well known that, in their structure, hip prostheses form a ball-and-socket joint, with a female component reconstituting the cotyloid cavity in the hip bone (ilium), and a male component carrying a spherical head fixed at the end of a neck, the neck being joined to a shaft anchored in the medullary cavity of the femur. The invention concerns this latter component, the femoral component, and refers to the cotyloid component only as far as concerns its complementarity with the femoral component.

It will be understood that as the prosthesis is intended to be substituted for the natural joint of the head of the femur in the cotyloid cavity of the hip bone in conditions as close as possible to the healthy natural joint, the elements of the prosthesis components which take the place of the bone elements of the joint will be designated by the same names as the bone elements, their orientations and dimensions will, unless otherwise indicated, be similar to those of the elements of the corresponding natural joint, and the reference to their spatial positions will be given to their implanted position.

More particularly it will be considered that, relative to the general axis of the femur, considered as approximately straight and vertical, the head is offset in a frontal plane on the internal side at the end of the neck, orientated in this front plane to form an angle of about 135° with the axis of the femur, and that the axis of the neck connects with the axis of the femur through a curvature of the axis of the medullary canal in the region of the trochanter, this axis forming substantially the neutral axis of the femur considered as a load-bearing member.

There are two main types of femoral component for hip prostheses, the components which are sealed with a polymerised organic cement in the medullary cavity and the components which are jammed by force into this cavity, the growth of the spongy bone in contact with the surface of the shaft, suitably formed with numerous cavities and projections, providing an anchorage by interpenetration of the bone and the surface of the shaft.

The components which are sealed by means of an organic cement have a certain number of disadvantages; during the installation of the prosthesis, it is necessary to wait, after the sealing of the shaft, until the cement has acquired sufficient resistance by polymerisation before proceeding with the intervention. The setting of the cement by polymerisation releases some heat and it leads to a certain swelling of the cement which sometimes causes distressing pains. The presence of the cement is not favourable to the growth of the spongy bone, and it can happen that in the course of time the sealed shaft works loose, which requires a fresh intervention. Then, during a new installation of a prosthesis, the elimination of the previous cement can be difficult.

It has been recommended to use femoral components held by jamming in the medullary cavity. The shaft has a radius of curvature different from that of the axis of the medullary cavity at the connection with the neck of the femur. When this shaft has been driven into the medullary cavity, it bears on the walls of this cavity in three zones: at the two ends, the point of the shaft and the root of the neck it bears through its most concave internal generatrix, and in the region of the trochanter it bears through its dorsal generatrix, in an intermediate zone between the ends, the dorsal generatrix being opposed to the internal generatrix in the frontal plane. As already indicated, the exterior face of the shaft has a surface condition, sometimes called madreporic, with cavities and projections, to encourage the penetration and accretion of growing spongy bone. Other femoral components are massive and jam for all of their length. Their shaft is generally longer than that of those previously described.

Study of the behaviour of such femoral components after installation has shown that the locking thus obtained is not without disadvantages. The stress of the shaft creates pain for the patient. In other respects, it has become evident that while locking against a rotation of the shaft is indispensable, good functioning of the prosthesis involves a longitudinal suppleness, with a play of the order of a millimeter. Indeed if the metal, generally titanium for reasons of weight, biological compatibility, chemical inertia and suitability for machining, has a modulus of elasticity removed to the least extent from that of the cortical bone, it does not reproduce the suppleness and shock absorption of the natural bone in the region of the trochanter and the neck. Now, with jamming at three points, suppleness is obtained by longitudinal displacements of the shaft, which cause clearances at the bearing zones, but these clearances do not sufficiently ensure locking against rotation. Massive femoral components do not have the required suppleness.

It has been proposed also (EP-A-0 131 178) to provide a femoral component with a pin, carrying the head of the joint, which narrows from the top towards the bottom, and an assembly of wedge pieces which are freely guided in channels cut in the pin. The friction between wedge pieces and channels is much weaker than the friction which arises between the bone and the exterior surfaces of the wedge pieces, which are adapted to be adherent. Loading the pin brings about a spreading apart of the wedge pieces; if the medullary cavity enlarges, the driving-in of the pin avoids a working loose between the bone and the component. The document states that the wedge angle of the pin is smaller than the angle of friction between the pin and the wedge pieces in such a manner as to prevent a to-and-fro play between these parts.

Such an arrangement prevents perfectly any rotational play of the component relative to the bone, but at the cost of the suppression of all longitudinal suppleness. The disadvantages of the massive components are found again.

BRIEF SUMMARY OF THE INVENTION

To avoid these disadvantages, the invention proposes a femoral component of a hip prosthesis, intended to be implanted without cement and comprising a shaft adapted to be driven into the medullary cavity of the femur after removal of the head by cutting the neck, said shaft tapering to a lower end from an upper end from which projects a neck carrying an added spherical head suitable to form a ball-and-socket joint with a cotyloid component so as to reproduce the original natural joint, and having a curvature, in a frontal plane, corresponding to the natural connection of the axis of the neck to the axis of the diaphysis passing through the trochanter, the said shaft comprising a core from which the neck projects, said core being bounded substantially parallel to the frontal plane by two generally planar frontal faces extending at least in the region of the trochanter, and two packing pieces adapted to embrace the core, along the said frontal faces, by means of complementary bearing faces, the said packing pieces also having external convex faces adapted to fit the medullary cavity, these convex faces possessing a surface condition suitable for bonding by penetration of spongy bone as it grows, as a result of which the core is blocked against rotation despite being capable of a longitudinal elastic play relative to the femur of an order of magnitude corresponding to the play by elastic flexing of the original natural bone.

Although the packing pieces can settle in a definitive position, the core can preserve an appreciable play in the longitudinal direction by sliding between the bearing faces of the packing pieces, which prevent any rotation. The packing pieces are also referred to in the art as medullary wedging members. The shaft as a whole, and more precisely the core, is not locked against arcuate flexing, which overcomes one of the causes of suffering for the patient. In other respects, the core rests, in the longitudinal direction, on some bone, through the majority of its surface exterior to the frontal plane faces, which enables one to find again a suppleness and shock absorption comparable to those of the original bone.

Preferably also the frontal faces of said core and the bearing faces of the packing pieces have complementary guide means, these guide means being suited to direct said packing pieces relative to said core in the medullary cavity. The core being installed first, the insertion of the packing pieces and their taking-up of position are facilitated by the guide means. According to an advantageous embodiment, each packing piece is provided with a cavity open at the upper part and closed along the convex face by a perforated wall. Some grafts of spongy bone can be inserted in the cavity for the purpose of knitting together, by growth, to the spongy bone which lines the medullary cavity, through the perforations of the convex wall of the packing piece.

BRIEF DESCRIPTION OF THE DRAWINGS

The characteristics and advantages of the invention will be further evident from the following description, by way of example, with reference to the accompanying drawings, in which.

DESCRIPTION OF THE PREFERRED EMBODIMENTS

Figure 1:
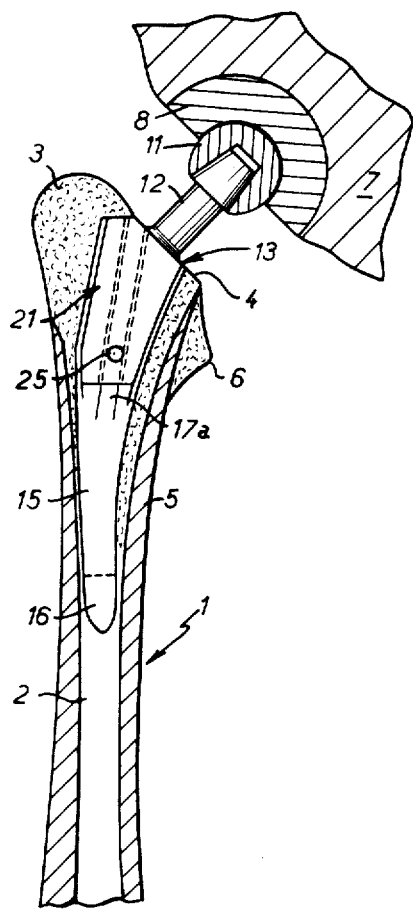
FIG. 1 represents schematically a hip prosthesis with a femoral component according to the invention.

As shown in FIG. 1, a hip prosthesis comprises, implanted in the femur 1, a femoral component 10 as a whole with a shaft 15 inserted in the medullary canal 2 of the femur 1. Projecting from the upper end 13 of the shaft 15, a cylindrical neck 12 carries a head 11, the neck 12 and head 11 being dimensioned to take the place of the original neck and head. The head 11, spherical, swivels in a cotyloid component 8, fixed (generally by screwing) in the hip bone 7.

The femur 1 comprises, at its upper end, masses of spongy bone, comprising: the great trochanter 3, projecting away from the neck, in a frontal plane which corresponds to the plane of the drawing; the lesser trochanter 6 which projects in this frontal plane on the internal face of the femur (i.e. the face which is closest to the femur of the other thigh). The cortical shank of the femur 1 widens out and terminates in a thin wall, the medullary cavity 2 being also flared and being lined towards its upper end with spongy bone, notably the calcar 4 towards the internal edge of the medullary cavity near the lesser trochanter 6.

Figure 2:
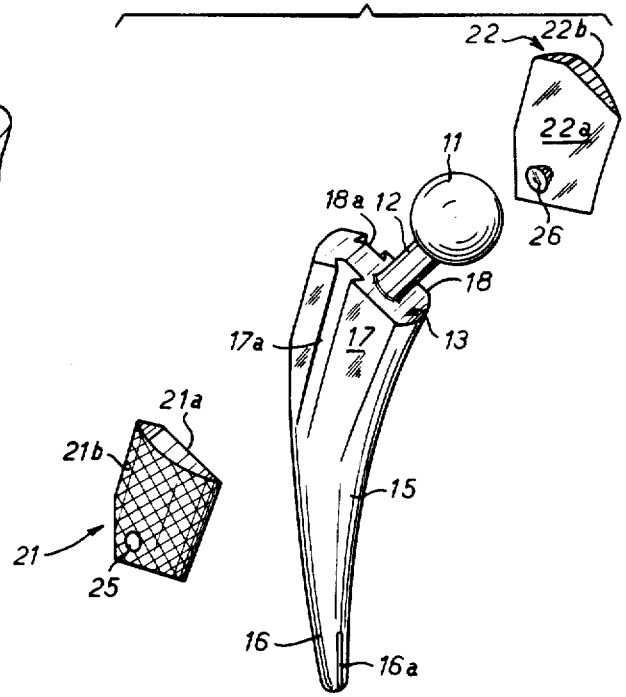
FIG. 2 is an exploded perspective view of the femoral component of FIG. 1, comprised of one core and two packing pieces.

According to the preferred embodiment, more apparent in FIG. 2, the femoral component 10 comprises a core of forged titanium of grade TA6V, which constitutes the most important part of the shaft 15 of the femoral component 10. This core tapers from its upper face to its lower end 16 and presents two frontal faces 17 and 18, approximately parallel to the frontal plane which contains the longitudinal axis of the shaft, with however a small angle of convergence towards the end 16 of the shaft. This convergence is too small to be represented clearly. If FIG. 1 represents a right articulation of the patient viewed from the front, the faces 17 and 18 will be respectively anterior and posterior. One will note that, in FIG. 2, the posterior face 18 is hidden.

The lower end 16 of the core has a slot 16a following the frontal plane, to confer elasticity in a sagittal direction, perpendicular to the frontal plane; this arrangement permits longitudnal displacements of the shaft 15, in the confined part of the medullary cavity, the nose pieces of the core, on either side of the slot 16a, forming a spring bearing on the wall.

Packing pieces 21 and 22, also of forged titanium, come to abut by means of planar bearing faces 21a and 22a, on the planar frontal faces, respectively the anterior face 17 and the posterior face 18, of the core 15. The packing pieces 21 and 22 moreover have convex external faces 21b and 22b, which in the coupled position come to complete a form which is complementary to the funnel shape of the medullary cavity.

Like practically all the shafts of femoral components, the shaft 15 is curved to connect the axis of the neck 12 to the axis of the medullary cavity, reproducing the natural arrangement of the joint. The curvature is essentially in the frontal plane and is concave for the internal generatrix.

Figure 3:
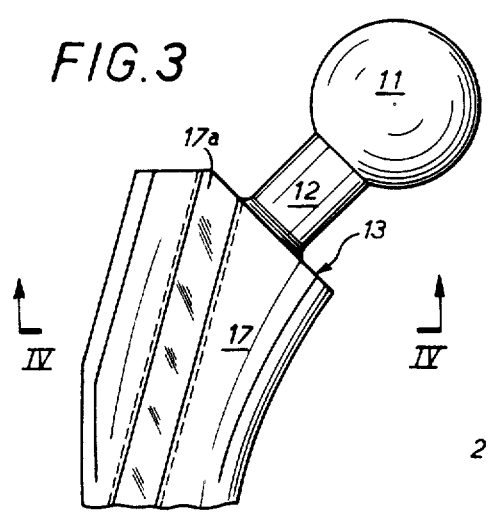
FIG. 3 is a view of the upper part of the core of the femoral component of the invention.
Figure 4:
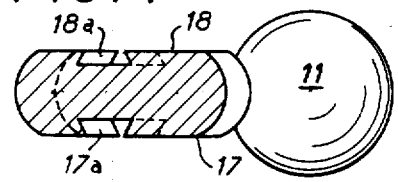
FIG. 4 is a section on line IV—IV of FIG. 3.

As can be seen better in FIGS. 3 and 4, in the frontal faces 17 and 18 of the core 15 are machined two dovetail-shaped channels 17a and 18a, straight and opening into the upper face 13 of the core 15 at the level of the neck 12. These dovetail-shaped channels are intended to guide the packing pieces 21 and 22 during their installation.

The bases of these channels 17a and 18a are strictly parallel, such that their depth reduces gently from the face 13 towards the end 16 of the shaft, because of the gentle convergence of the faces 17 and 18.

Figure 5A:
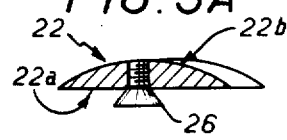
FIGS. 5A and 5B represent in section, corresponding to the section of FIG. 3, the front and rear packing pieces of the femoral component.
Figure 5B:
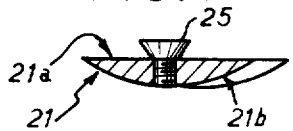

As can be seen in FIGS. 5A and 5B, the packing pieces 21 comprise studs 25 and 26 respectively, with a frustoconical head and threaded shaft, made of forged titanium, the profile of the frustoconical heads of the studs 25 and 26 fitting into the dovetail-shaped channels 17a, 18a to guide the lower ends of the packing pieces 21 and 22.

The protrusion of these studs 25 and 26 is at least equal to the depth of the channels 17 and 18 at their opening into the face 13 of the core 15. Thus the end faces of the studs 25 and 26 come into contact with the base of the channels 17 and 18 which are, as stated above, strictly parallel, such that the guiding of the packing pieces by the studs is achieved without jamming.

It is preferred that the exterior surface of the core 15, and the bearing faces 21a and 22a of the packing pieces 21 and 22, should be treated by nitridation, to improve the physiological compatibility of the prosthesis.

The external convex faces 21b and 22b of the packing pieces 21 and 22 have been rendered rough, with pores of 0.2 to 0.5 mm, either by microball treatment or by a covering of sintered titanium powder or by pulverisation with a plasma torch.

The fitting of a hip prosthesis has two aspects, an aspect of surgical intervention which in itself is outside the scope of the invention, and an aspect of mechanical procedure which has determined the structure of the article of the invention. It is within this point of view of mechanical procedure that the description of the installation of the prosthesis will be given. It will be understood nevertheless that the procedure of installation depends on organic reactions.

The installation of the cotyloid component will only be mentioned in passing, given that it is outside the scope of the invention, but that the installation of the femoral component is necessarily dependent on it.

To fit the femoral component, the neck is cut flush with the calcar 4 at an angle of about 45° relative to the general direction of the femur, and the medullary canal is cleared to make a cavity in the shape of the shaft 15 of the femoral component 10, the size of which has been determined by previous radiographic examinations, with a view to driving-in of the shaft.

The core 15 is then forced into place by "impaction", according to the expression of the surgical art, until its upper end face 13 comes substantially to the level of the section of the neck of the femur, this installation being carried out in a frontal plane.

Packing pieces which correspond best to the form of the medullary cavity are then chosen from the set of anterior packing pieces 21 and posterior packing pieces 22 of increasing convexity. The studs 25 and 26 of these packing pieces 21 and 22 are engaged respectively in the entry of the channels 17a and 18a of the core 15, and the packing pieces are conveyed to their definitive position by "impaction".

It will be noted that during the installation of the packing pieces 21 and 22, the orientation of these packing pieces relative to the core 15 varies, such that the packing pieces together can follow a curved trajectory corresponding to the curvature of the core, even though the guide channels are rectilinear.

As stated above, the convex surfaces 21b and 22b of the packing pieces 21 and 22 are rough and madreporic to facilitate the connection with the growing spongy bone. In another embodiment, the packing pieces are grooved with channels opening into the upper face, and the convex surfaces 21b and 22b are constituted by wire gauzes of titanium wire, welded at their periphery to the body of the packing pieces. It is then possible to insert into the packing pieces some grafts of spongy bone, which will grow and come to bind to the walls of the medullary cavity across the wire gauze. The immobilisation of the packing pieces in the upper part of the femur is thus assured for long periods.

It will be understood that the core which provides the bearing faces for the packing pieces, by virtue of the base of the channels acting on the terminal faces of the studs, can move longitudinally on a millimetric path, which confers on the prosthesis a suppleness and shock absorption comparable to that of the healthy joint.

Obviously the invention is not limited to the Example described in detail but embraces the variants within the limits of the scope of the claims.

I claim:

1. A femoral component of a hipprosthesis, intended to be implanted without cement and comprising a shaft adapted to be driven into a medullary cavity of a femur after removal of the head by cutting the neck, the shaft tapering to a lower end from an upper end, a neck projecting from the upper end of the shaft, and a head carried on the neck suitable to form a ball-and-socket joint with a cotyloid component, said shaft having a longituidnal axis and comprising a core from which said neck projects, said core being bounded by generally planar front and rear plane bearing faces extending parallel to a frontal plane which contains said longitudinal axis, at least along a trochanter region part of said core there being disposed two packing pieces having generally planar complementary bearing faces in sliding relation with said front and rear plane bearing faces on said core, sid packing pieces also having external convex faces adapted to fit the medullary cavity, said external convex faces having a nonsmooth surface suitable for bonding by ingrowth of spongy bone, said front and rear faces of said core and said bearing faces of said packing pieces having complementary guide means, said guide means being suited to direct movement of said packing pieces relative to said core in the medullary cavity, said guide means comprising a dovetail-shaped channel in each of said front and rear faces of said core, and a stud with a frustoconical head, projecting from the bearing faces of each of said packing pieces into the respective channels thereby allowing longitudinal elastic play of said prosthesis while preventing rotation of the core relative to the femur.

2. A femoral component according to claim 1, wherein said core has an upper and lower end and has at its lower end a slot which extends parallel to the front and rear plane bearing faces.

3. A femoral component according to claim 1, wherein said packing pieces have an upper part and a lower part and said stud is located towards the lower part of the bearing face of each of said packing pieces.

4. A femoral component according to claim 1, wherein the height of said frustoconical stud head is at least equal to the depth of the corresponding channel in the core.

5. A femoral component according to claim 1, wherein each packing piece is provided with a cavity open at the upper part of the packing piece and the nonsmooth surface of the external convex face is defined by a perforated wall.

6. A femoral component of a hip prosthesis comprising a shaft and adapted to be implanted into a meduallary cavity of the femur after removal of its head, said shaft tapering from an upper end to a lower end, a neck projecting from the upper end of said shaft, and a head carried on said neck for forming a ball-and-socket joint with a cotyloid component, said shaft having a longitudinal axis and comprising a core from which said neck projects, said core being bounded by generally planar front and rear plane bearing faces extending parallel to a frontal plane which contains said longitudinal axis, at least along a trochanter region part of said core there being disposed two packing pieces having generally planar complementary bearing faces in sliding relation with said front and rear plane bearing faces of said core, said packing pieces also having external convex faces complementary to the medullary cavity, said external convex faces having a nonsmooth surfaces condition suitable for bonding by ingrowth of spongy bone thereby allowing longitudinal elastic play of said prosthesis while preventing rotation of the core relative to the femur.

7. A femoral component according to claim 6, further comprising complementary guide means on each of the front and rear plane bearing faces of said core and on said packing pieces for guiding movement of said core relative to said packing pieces along said bearing faces.

8. A femoral component according to claim 7, wherein said guide means permits longitudinal movement of said core relative to said packing pieces.

9. A femoral component according to claim 8, wherein said guide means permits both longitudinal and angular movement of said core member relative to said packing pieces and parallel to said front plane.

10. A femoral component according to claim 7, wherein said guide means comprisies a channel in each of said front and rear plane bearing faces of said core and a stud with a head projecting from the bearing face of each of said packing pieces and received in a respective channel in said core.

11. A femoral component according to claim 10, wherein said guide means includes means for retaining each of said heads in its respective channel.

12. A femoral component of a hip prosthesis adapted to be implanted without cement and comprising a shaft adapted to be driven into a medullary cavity of the femur after removal of its head by cutting its neck, said shaft tapering from an upper end to a lower end, a neck projecting from the upper end of said shaft, and a head carried on said neck for forming a ball-and-socket joint with a cotyloid component, said shaft having a longitudinal axis and comprising a core from which said neck projects, said core being bounded by generally planar front and rear plane bearing faces extending parallel to a frontal plane which contains said longitudinal axis, said core having medial and lateral faces extending between said front and rear planes, at least along a trochanter region part of said core there being disposed two packing pieces having generally planer complementary bearing faces in sliding relation with said front and rear plane bearing faces on said core, said packing pieces having external convex faces complementary to the medullary cavity, said external convex faces having a nonsmooth surface suitable for bonding by ingrowth of spongy bone, said medial and lateral faces of said core being devoid of contact with said packing pieces thereby allowing longitudinal elastic play of said prosthesis while preventing rotation of the core relative to the femur.

13. A femoral component according to claim 12, further comprising complimentary guide means on each of the front and rear plane bearing faces of said core and on said packing pieces for guiding movement of said core relative to said packing pieces along said bearing faces.

* * * * *

UNITED STATES PATENT AND TRADEMARK OFFICE
CERTIFICATE OF CORRECTION

PATENT NO. : 4,718,915
DATED : Jan. 12, 1988
INVENTOR(S) : Jean-Alain Epinette

It is certified that error appears in the above-identified patent and that said Letters Patent is hereby corrected as shown below:

<u>In The Specification</u>

Col. 4, line 42, "longitudnal" should read --longitudinal--.

<u>In The Claims</u>

Col. 6, line 21, claim 1, "hipprosthesis" should read --hip prosthesis--.

Col. 6, line 29, claim 1, "longituidnal" should read --longitudinal--.

Col. 6, line 37, claim 1, "sid" should read --said--.

Col. 8, line 33, claim 13, "complimentary" should read --complementary--.

Signed and Sealed this

Twenty-eighth Day of June, 1988

Attest:

DONALD J. QUIGG

Attesting Officer

Commissioner of Patents and Trademarks